(12) United States Patent
Lin et al.

(10) Patent No.: US 7,416,093 B2
(45) Date of Patent: Aug. 26, 2008

(54) CONTAINER WITH CONTROLLED-OPENING LID

(75) Inventors: Yvonne Song Lin, New York, NY (US); Douglas Bruce Winner, Newtown, CT (US)

(73) Assignee: Punch Products USA, Inc., Rahway, NJ (US)

( * ) Notice: Subject to any disclaimer, the term of this patent is extended or adjusted under 35 U.S.C. 154(b) by 333 days.

(21) Appl. No.: 11/053,114

(22) Filed: Feb. 7, 2005

(65) Prior Publication Data

US 2006/0175331 A1 Aug. 10, 2006

(51) Int. Cl.
B65D 51/18 (2006.01)
A47G 19/22 (2006.01)
E05F 1/08 (2006.01)

(52) U.S. Cl. .................. 220/254.5; 220/254.3; 220/714; 220/715

(58) Field of Classification Search .................. 220/714, 220/715, 254.1, 254.3, 254.5, 254.6, 264, 220/262; 16/305, 307, 54, 342; 222/533, 222/517, 472, 556, 470, 471
See application file for complete search history.

(56) References Cited

U.S. PATENT DOCUMENTS

| | | | |
|---|---|---|---|
| 2,056,170 A | * | 10/1936 | Deschner ..................... 222/109 |
| 2,272,867 A | * | 2/1942 | Cobel .......................... 222/473 |
| 2,622,420 A | | 12/1952 | Rice |
| 3,647,224 A | | 3/1972 | Klein |
| 3,847,311 A | | 11/1974 | Flores et al. |
| 3,952,365 A | | 4/1976 | Grisebach |
| 3,964,631 A | | 6/1976 | Albert |
| 3,967,748 A | | 7/1976 | Albert |
| 3,972,444 A | | 8/1976 | Adams |
| 4,094,433 A | | 6/1978 | Numbers |
| 4,099,642 A | | 7/1978 | Nergard |
| 4,133,446 A | | 1/1979 | Albert |
| 4,165,013 A | | 8/1979 | Lutz |
| 4,212,408 A | | 7/1980 | Valenzona |
| 4,276,992 A | | 7/1981 | Susich |
| 4,290,168 A | | 9/1981 | Binge |
| 4,303,173 A | | 12/1981 | Nergard et al. |
| 4,328,639 A | | 5/1982 | Cotey |
| 4,781,773 A | * | 11/1988 | Instance ....................... 156/69 |
| 4,782,932 A | | 11/1988 | Janson |
| 4,914,799 A | | 4/1990 | Kyle |

(Continued)

FOREIGN PATENT DOCUMENTS

DE 10010307 A1 3/2002

(Continued)

*Primary Examiner*—Robin Hylton
(74) *Attorney, Agent, or Firm*—Jones Day

(57) ABSTRACT

A container having a controlled-opening lid includes a container body with an open end providing access to an interior space configured and dimensioned for receiving user-supplied contents, and a lid member configured and dimensioned to cover the open end of the container body when in a first position and permit access to the interior space when in a second position. A hinge is configured to move the lid member from the first position to the second position, the hinge including at least one damping mechanism for damping a biasing force provided by the hinge when the lid member moves from the first position to the second position. The container may be a beverage container or a physician's desk container for storing medical implements.

27 Claims, 11 Drawing Sheets

U.S. PATENT DOCUMENTS

| | | | |
|---|---|---|---|
| 4,925,051 A | 5/1990 | Herbst | |
| 4,936,433 A | 6/1990 | Kyle | |
| 4,946,131 A | 8/1990 | Weyand | |
| 4,949,865 A | 8/1990 | Turner | |
| 4,962,838 A | 10/1990 | Clancey | |
| 4,989,713 A | 2/1991 | Janson | |
| 5,118,014 A | 6/1992 | Hestehave et al. | |
| 5,180,132 A * | 1/1993 | Pearson et al. | 248/362 |
| 5,186,353 A | 2/1993 | Ramsey | |
| 5,203,467 A | 4/1993 | Tucker | |
| 5,222,623 A | 6/1993 | Eger et al. | |
| 5,239,731 A | 8/1993 | Lu | |
| 5,402,904 A | 4/1995 | Close | |
| 5,409,131 A | 4/1995 | Phillips et al. | |
| 5,425,157 A | 6/1995 | Chang | |
| 5,477,980 A | 12/1995 | Chaffin | |
| 5,485,938 A | 1/1996 | Boersma | |
| D377,758 S | 2/1997 | Valley | |
| 5,706,972 A | 1/1998 | Sousa | |
| 5,732,135 A | 3/1998 | Weadon et al. | |
| 5,739,758 A | 4/1998 | Driska et al. | |
| 5,771,539 A | 6/1998 | Wahlstedt et al. | |
| 5,875,941 A | 3/1999 | Hsu | |
| 5,881,150 A | 3/1999 | Persson | |
| 6,062,419 A | 5/2000 | Kruger et al. | |
| 6,085,384 A | 7/2000 | Bivens | |
| 6,098,834 A | 8/2000 | Hatsumoto et al. | |
| 6,175,085 B1 | 1/2001 | Tippner et al. | |
| 6,195,431 B1 | 2/2001 | Middleton | |
| 6,325,236 B1 | 12/2001 | Wong | |
| 6,373,039 B2 | 4/2002 | Lee | |
| 6,557,717 B1 | 5/2003 | Keck | |
| 6,702,137 B1 * | 3/2004 | Kowa et al. | 220/254.5 |
| 7,195,137 B2 * | 3/2007 | Belcastro | 222/484 |
| 2002/0092581 A1 | 7/2002 | Belcastro | |
| 2005/0229788 A1 * | 10/2005 | White | 99/323 |

FOREIGN PATENT DOCUMENTS

| | | |
|---|---|---|
| JP | 2001151257 A | 11/1999 |
| JP | 2000005071 A | 1/2000 |
| WO | WO 9920162 A1 | 4/1999 |

\* cited by examiner

CONTAINER WITH CONTROLLED-OPENING LID

FIELD OF THE INVENTION

The present invention relates to containers, and, more particularly, to a container having an operable lid or cover with a damping mechanism that provides for controlled opening of the lid or cover member when access to the container interior is desired. In one preferred embodiment, the present invention relates to a beverage container with a drinking aperture covered by a controlled-opening lid employing a damping mechanism. In another preferred embodiment, the present invention relates to a physician's desk container for storing medical implements having a controlled-opening lid employing a damping mechanism.

BACKGROUND OF THE INVENTION

Drinking mugs and beverage containers have been adapted over the years to facilitate beverage consumption during travel activities such as walking or riding in an automobile, bus, train or airplane. Traditional coffee mugs are not suitable for drinking beverages while traveling because they easily spill their contents, and are often heavy and prone to breakage if dropped. These problems coupled with the public's desire to save time by consuming their beverages while traveling has led to the increased popularity of beverage containers suitable for use during travel. Commuters often fill such containers with their morning coffee, tea, juice, etc. to consume during their journey to work each day. These containers, as known in the art, usually consist of an insulated container body, or body member, for maintaining the temperature of the contained beverage and a lid member with a smaller drinking aperture that fits securely over the container member to minimize spillage during drinking. See, e.g., U.S. Pat. No. 5,249,703 to Karp, U.S. Pat. No. 5,918,761 to Wissinger, and U.S. Design Pat. No. 399,392 to Husted.

Many prior art travel mugs have a small cover over the drinking aperture which must be manually opened by the user's hand or mouth when the user wishes to take a drink. Such containers often include an air-tight seal between the cover and the drinking aperture in order to maintain the temperature of the beverage. But such sealing connections may often require substantial user effort to open and/or properly close the lid because the air-tight seal must be formed or broken in each instance. If the container is full, undesirable spillage may occur when the air-tight seal is broken between the cover and aperture because the cover may unexpectedly and abruptly open in response to the user-applied force. This can defeat the purpose of the lid entirely.

Still other prior art beverage containers include a cover over the drinking aperture operated by a lever. In order to drink from the mug, the user must depress and hold the lever to gain access to the drinking aperture. But in order for the user to drink from this type of container, he or she must continuously depress the lever while holding the mug to his or her mouth, which may be awkward and/or uncomfortable.

Thus, there is a need for a container having a controlled-opening lid that prevents spillage of contents during opening and/or closing. The lid of such a container would open in a moderated fashion to produce a smooth, pleasing effect in response to a minimal amount of user effort.

SUMMARY OF THE INVENTION

In a preferred embodiment, the present invention relates to a container with a controlled-opening lid comprising a container body having an open end providing access to an interior space configured and dimensioned for receiving user-supplied contents and a lid member configured and dimensioned to cover the open end of the container body when in a first position and permit access to the interior space when in a second position. A hinge is operable to move the lid member from the first position to the second position, the hinge including at least one damping mechanism for damping a biasing force provided by the hinge when the lid moves from the first position to the second position.

The hinge may include at least one torsional spring for providing a rotational biasing force to the lid member, and the damping mechanism may include damping grease applied to the housing or chamber that connects the lid to the lid member. The container may further include an activator configured and dimensioned to activate the hinge for moving the lid member from the first position to the second position in response to user input, which will allow the lid to open with a smooth, pleasing effect. The activator may be formed integrally with the lid member or, alternatively, may be formed on the container body.

The container and/or lid member may be formed of plastic, metal, a combination of plastic and metal, or any other suitable material. The container may be a beverage container formed of an insulating material, such as a travel mug, or a physician's desk container for storing medical implements.

In another preferred embodiment, the present invention relates to a container having a controlled-opening lid comprising a container body having an interior space configured and dimensioned for receiving user-supplied contents and a first lid member configured and dimensioned for attachment to the container body. The first lid member may have threads that mate with corresponding threads on the container body. The first lid member includes at least one aperture for providing access to the interior of the container body, a cover member configured and dimensioned to cover the aperture when in a first position and permit access to the aperture when in a second position, and a hinge configured and dimensioned to move the cover member from the first position to the second position. The hinge includes at least one damping mechanism for damping a rotational biasing force provided by the hinge when the cover moves from the first position to the second position. The cover member may include a suction cup connected to a bottom surface of the cover member for providing an air-tight seal between the cover member and the aperture. The container may also include a sealing ring disposed between the first lid member and the container body to aid in providing an air-tight seal between components.

The container may further comprise a second lid member having at least one aperture, a bottom portion of the second lid member configured and dimensioned for attachment to the container body and a top portion of the second lid member configured and dimensioned for attachment to the first lid member. An activator, which may be disposed on or integral with the cover member, the first lid member, or the second lid member, is configured and dimensioned to activate the hinge for smoothly moving the cover from the first position to the second position in response to user input.

The container and/or lid member may be formed of plastic, metal, a combination of plastic and metal, or any other suitable material. The container may be a beverage container formed of an insulating material, such as a travel mug, or a physician's desk container for storing medical implements.

DETAILED DESCRIPTION OF THE PREFERRED EMBODIMENT

Figure 1:
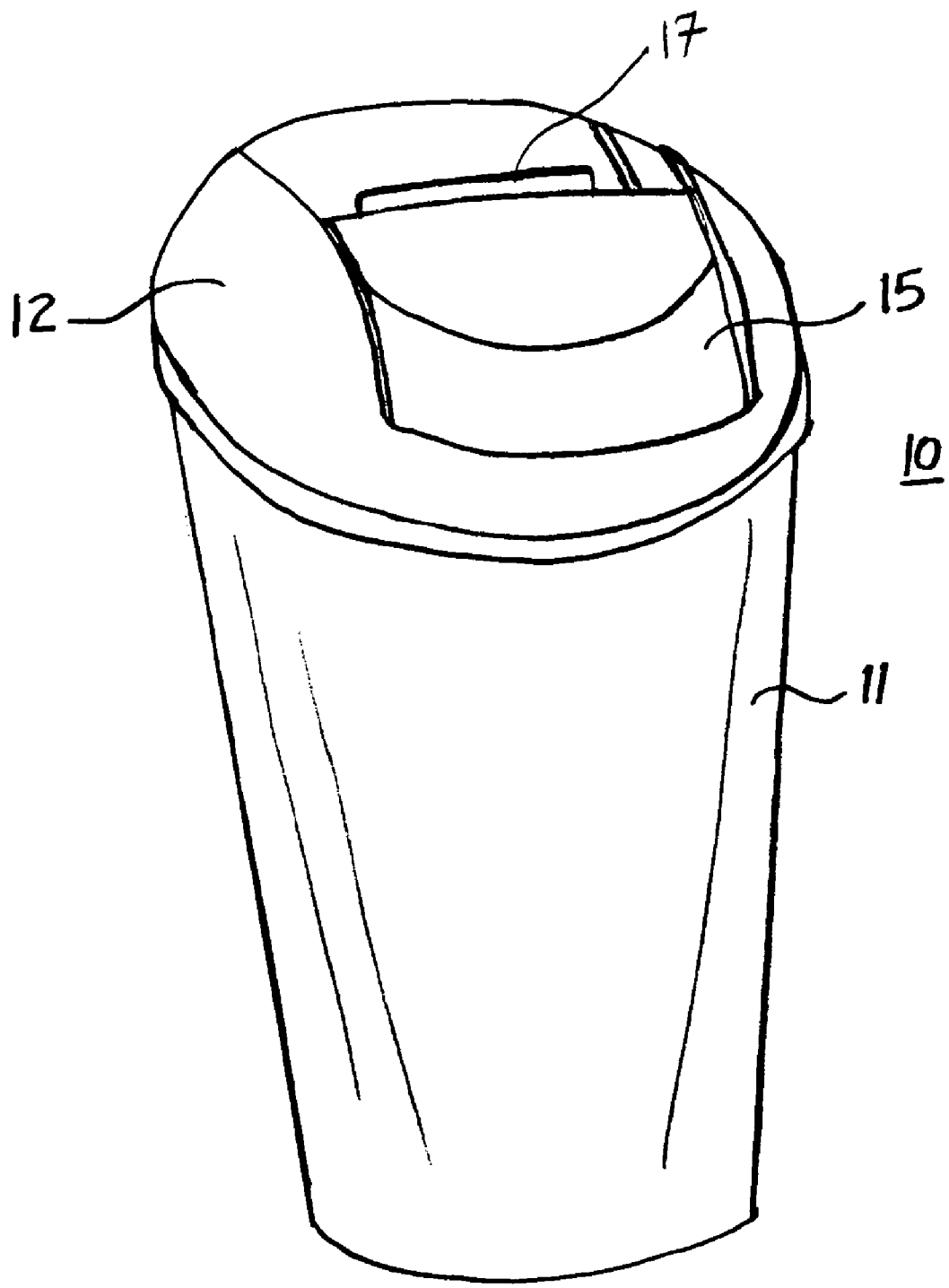
FIG. 1 is an isometric view of a container according to a first preferred embodiment of the present invention.
Figure 2:
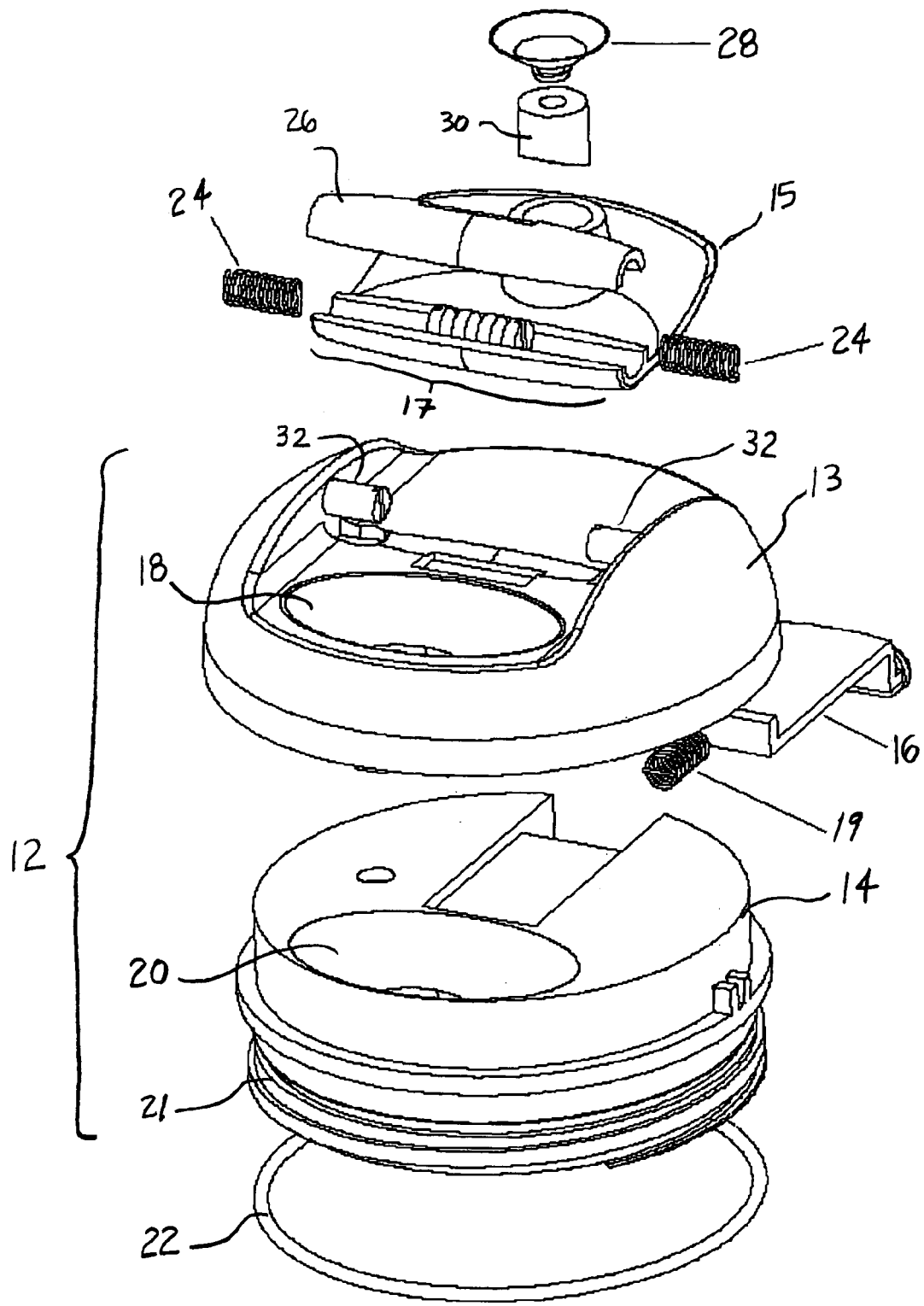
FIG. 2 is an exploded view of the lid member shown on the container of FIG. 1 prior to assembly.

Reference is now made to FIGS. 1-5 which show various views of a first embodiment of the present invention and components thereof. A container 10 includes a container body 11 having an interior space for receiving user-supplied contents, and a lid 12. Lid 12 may include first and second lid members 13, 14, respectively, as shown in the exploded view of FIG. 2. First and second lid member 13, 14 include aperture 18, 20, respectively, that allow access to the interior of container body 11. A cover member 15 is connected to lid member 13 via hinge 17 and rotates on an axis to cover aperture 18 when in a first closed position and permit user access to the interior of container body 11 through apertures 18, 20 when in a second open position. A sealing O-ring 22, formed of rubber or similar material, is preferably disposed between the bottom of second member 14 to provide an air-tight seal between lid 12 and container body 11.

An activator 16, such as a push button or lever, is provided for operating cover member 15. Activator 16 may situated on the second lid member 14, as shown, or, alternatively, may be included as part of container body 11, first lid member 13, or cover member 15. Hinge 17 contains at least one torsion spring 24 which act as the biasing force that rotates the cover 15 into an open position. The springs are covered by housing 26 that covers the hinge pins 32 connected to the second lid member 13. The hinge pins 32 are coated with damping grease to provide a damping effect between the cover 15 and the second lid member 13. The lid further comprises a cover 28, such as a suction member, which is connected to cover 15 via arm 30 and aids in providing an air-tight seal between container body 11 and lid 12. In an alternative embodiment, the damping mechanism may include a piston housed within a fluid-filled chamber.

Activator button 16 engages hinge 17 such that hinge 17 will operate to move cover 15 from the first closed position to the second open position upon user depression or triggering of activator 16. When the button is pressed in, the catch will release the cover and permit the rotational biasing force provided by hinge 17 to rotate cover 15 from the closed to the open position in a smooth, pleasing fashion. Activator button 16 is typically biased in place by a spring 19, which provides the restoring force necessary to push activator 16 back into position after user depression. Lid 12 will typically include a latch for securing the cover in the first closed position until the user wishes to access the interior of the container body 11. After opening cover 15, a user may push cover 15 closed and it will engage the latch to remain in the second closed position until activator 16 is pressed again. Lid 12 preferably has threads 21 for forming an air tight seal when the lid is screwed on to the body 11. In the case of a beverage container, this will prevent leakage or spillage of the beverage if the container happens to tip over or fall to the ground.

Figure 3A:
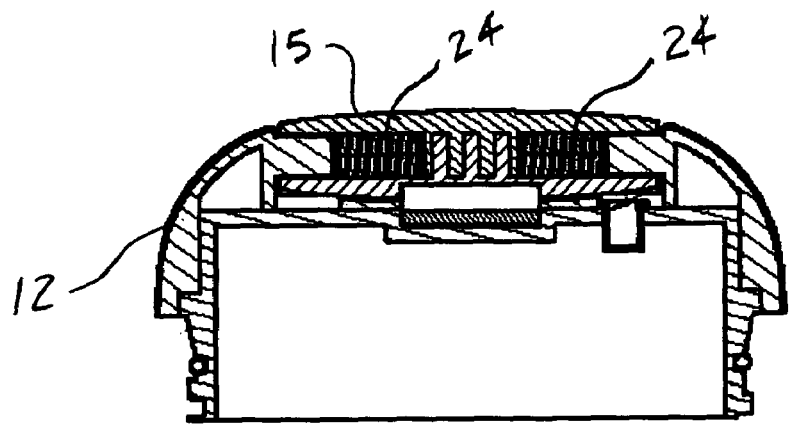
FIG. 3A is a front cross-section view of the lid member of FIG. 2 shown assembled.
Figure 3B:
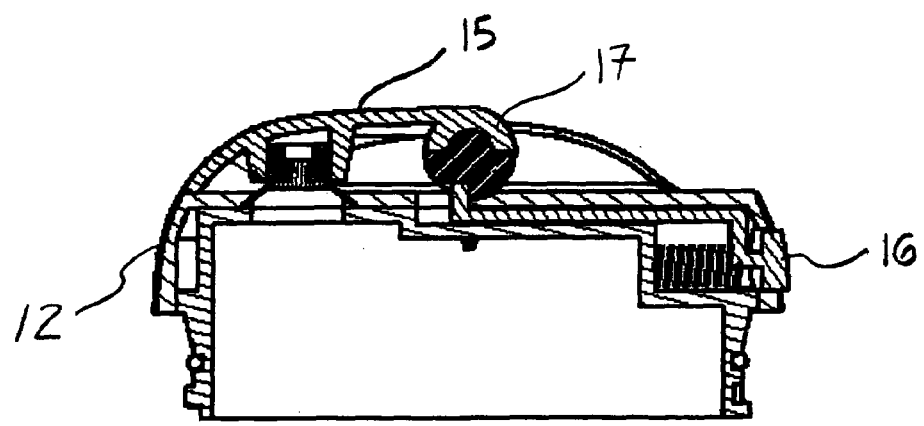
FIG. 3B is a side cross-section view of the lid member of FIG. 2 and its various components shown assembled.

A cross section of the lid 12 is depicted in FIGS. 3A-3B. Hinge 17 which attaches the cover to the mug lid will include a damping mechanism, as known in the art, configured and adapted to moderate the movement of cover 15 during opening. In a preferred embodiment, the dampening mechanism comprises hinge pins coated with damping grease, as known in the art, connecting the second lid member to the cover. Various other types of damping mechanisms are known in the art, such as the damping mechanism shown and described in U.S. Pat. No. 4,342,135 to Matsuo et al., which is hereby incorporated by reference.

As discussed above, hinge 17 preferably includes at least one torsional spring which applies a small amount of force to the cover of the mug lid. One end of the spring will press against the cover while the other end will be in constant contact with the mug lid. The natural biasing force of the spring will slowly force the cover to open when the catch holding the cover shut is released by pressing activator button 16. Hinge 17 provide for "one-way" damping, as known in the art, such that a user can move the cover back to the second first closed position over the drinking aperture without encountering any unwanted force. Alternatively, hinge 17 could incorporate a two way damping mechanism.

Figure 4:
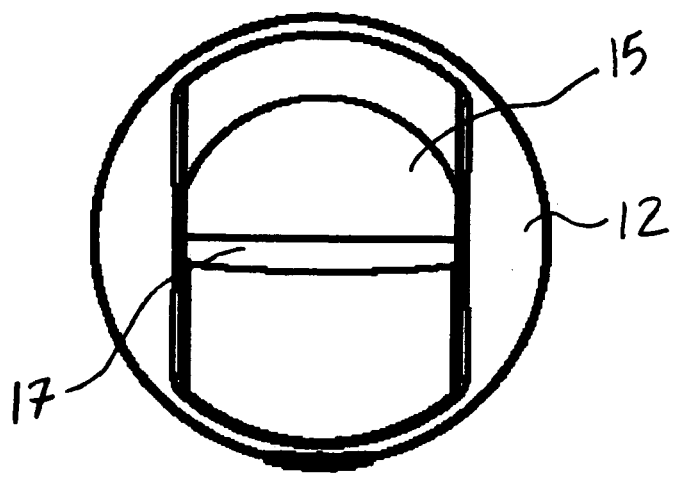
FIG. 4 is a top view of the lid member of FIG. 2 in a closed position.
Figure 5:
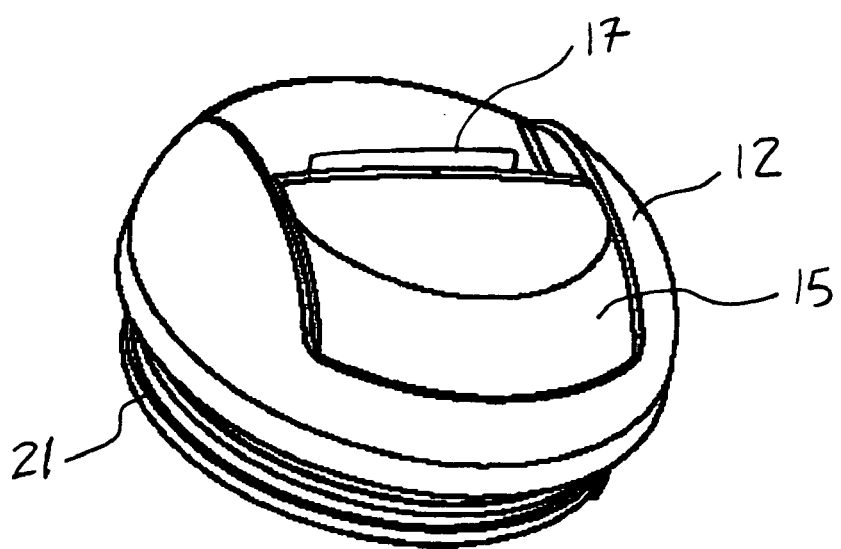
FIG. 5 is an isometric view of the lid member shown in FIG. 4.

Various views of lid 12 when closed are shown in FIGS. 4-5.

Figure 7:
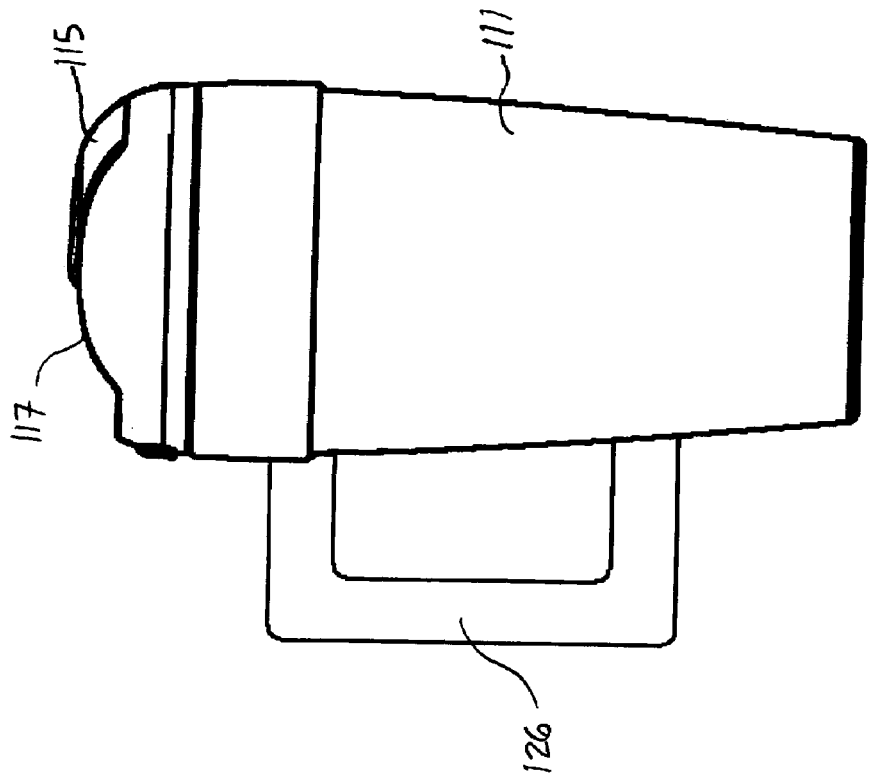
FIG. 7 is a side view of a container according to a another preferred embodiment of the present invention.
Figure 6:
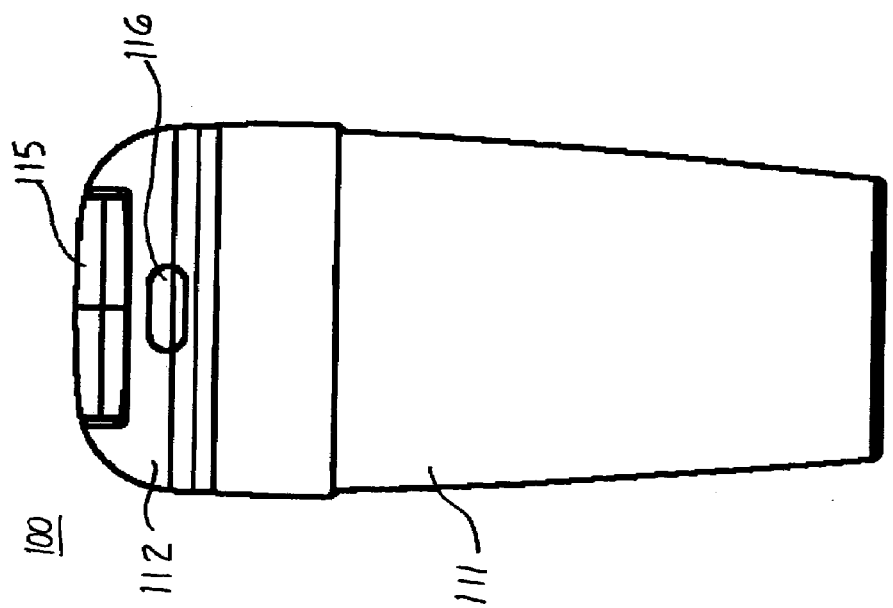
FIG. 6 is a rear view of a container according to a preferred embodiment of the present invention.
Figure 8:
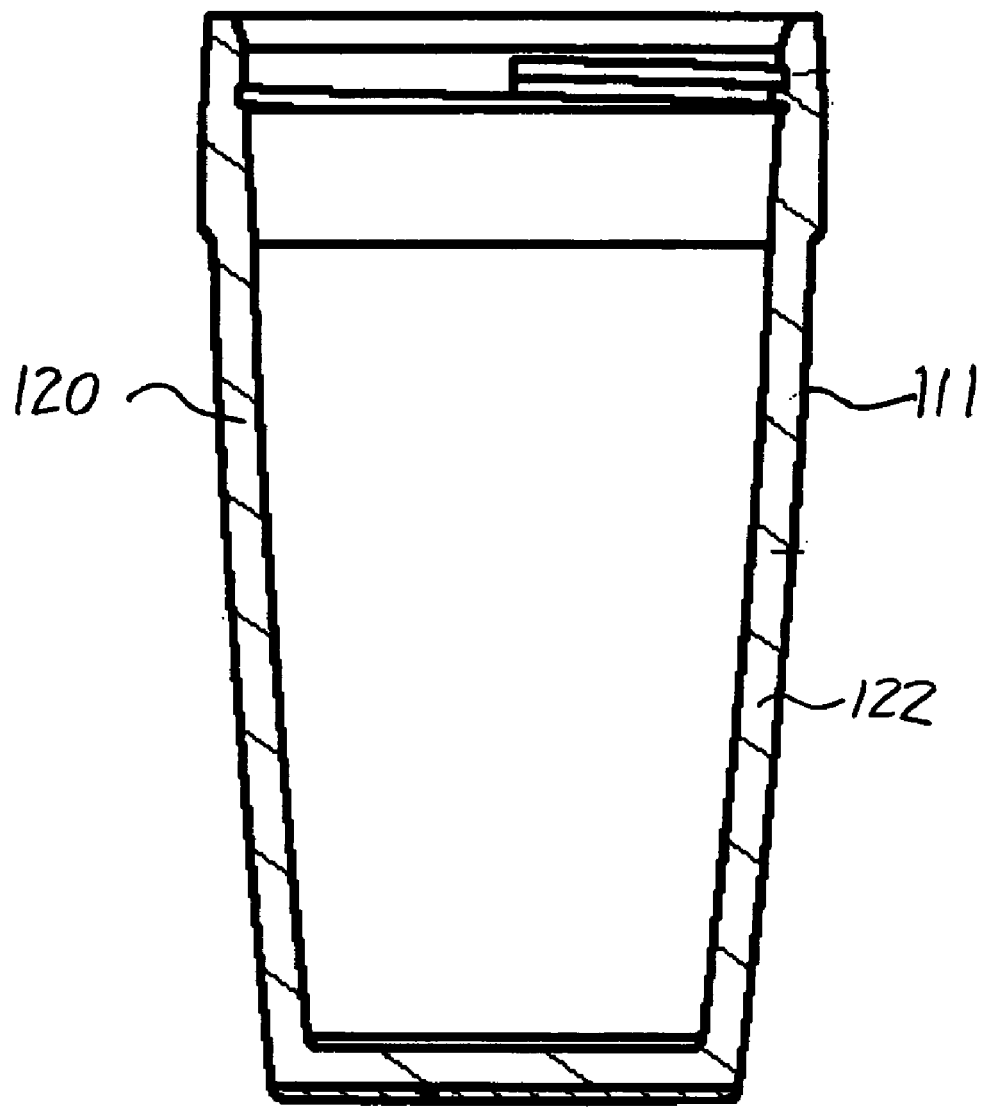
FIG. 8 is a cross-section view of a container formed of an insulating material, without a lid.

Reference is now made to FIGS. 6-7, which show front and side views of a beverage container 100 according to a preferred embodiment of the present invention. Beverage container 100 includes container body 111 having an open end and an interior space configured and dimensioned for receiving and storing a beverage, a lid 112 having a cover member 115, an activator button 116 for causing cover 115 to open in a controlled fashion by operation of a hinge 117 employing a damping mechanism. As shown in FIG. 8, container body 111 may have an insulated side wall 120, including an insulating layer 122, for maintaining the temperature of a stored beverage.

Figure 10:
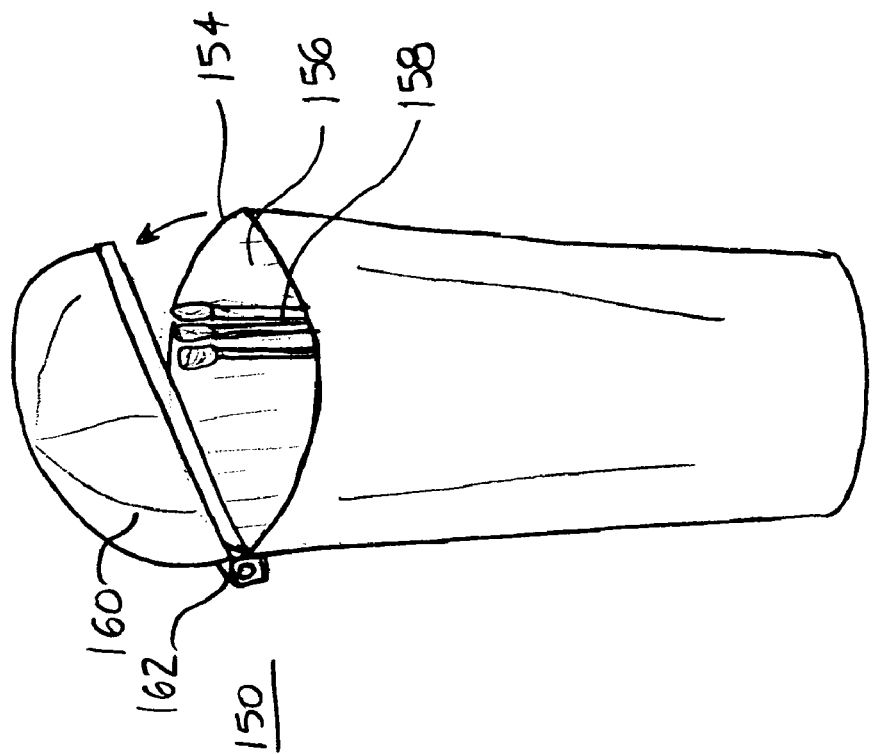
FIG. 10 is an isometric view of the container shown in FIG. 9 with the lid in the open position.
Figure 9:
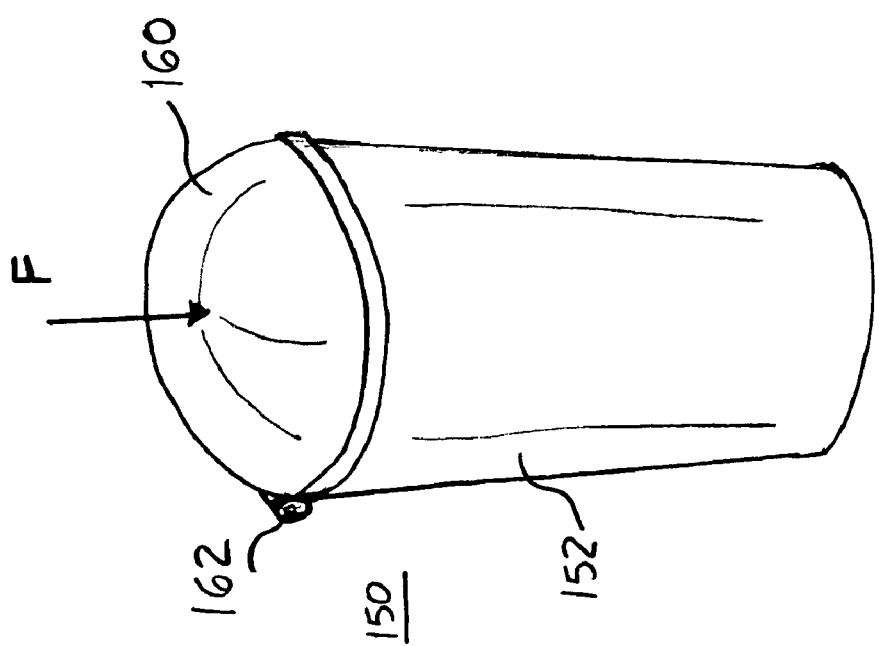
FIG. 9 is an isometric view of still another container according to another preferred embodiment of the present invention.

Reference is now made to FIGS. 9-10, which depict still another preferred embodiment of the present invention. A physician's desk container 150 includes a container body 152 having an open end 154 and an interior space 156 for storing medical implements 158, such as swabs, gauze, cotton balls, etc. A lid 160 is connected to body 152 via a damping hinge 162. In response to a user-applied force F to lid 160, hinge 162 is activated to slowly open lid 160 in a smooth, pleasing fashion to allow access to the interior of container 150. In alternative embodiments, an activator button may be incorporated into either lid 160 or body 152 to activate hinge 162 to open cover 160.

Figure 11:
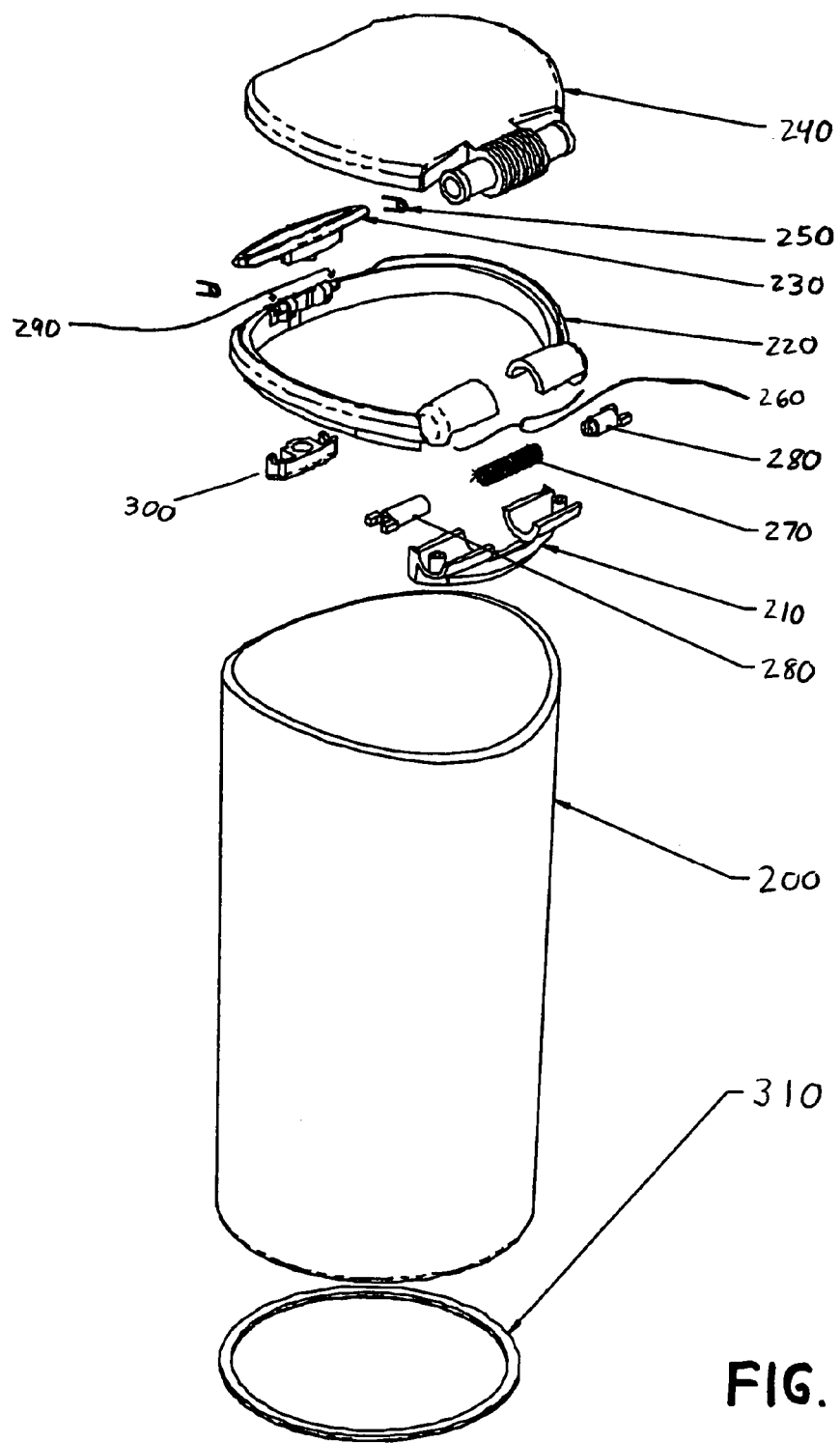
FIG. 11 is an exploded view of still another container according to another preferred embodiment of the present invention.

Reference is now made to FIG. 11 which depicts still another preferred embodiment of the present invention. A canister with dampened hinge includes a container body 200 connected to a lid pivot block 210 and lid member 220. The lid pivot block 210 is attached to the lid member 220 by two screws, not shown. The lid member has an activator 230 for releasing the cover 240. The activator 230 is biased in place by at least one spring 250 which provides the restoring force necessary to push activator 230 back into position after user depression. The cover 240 is attached to the lid member 220 with a hinge 260 comprising a torsional spring 270 and hinge pins 280 which are enclosed in a hole in the cover 240. The hinge pins 280 are preferably covered in damping grease which provide the damping effect between the cover 240 and the lid member 220. When depressed, the activator 230 rotates on latch pins 290 that are connected to the lid member 220. A latch pivot block 300 holds the activator 230 in place on the latch pins 290. The canister also includes a bottom ring 310 to prevent the canister from slipping on a smooth surface.

Figure 12:
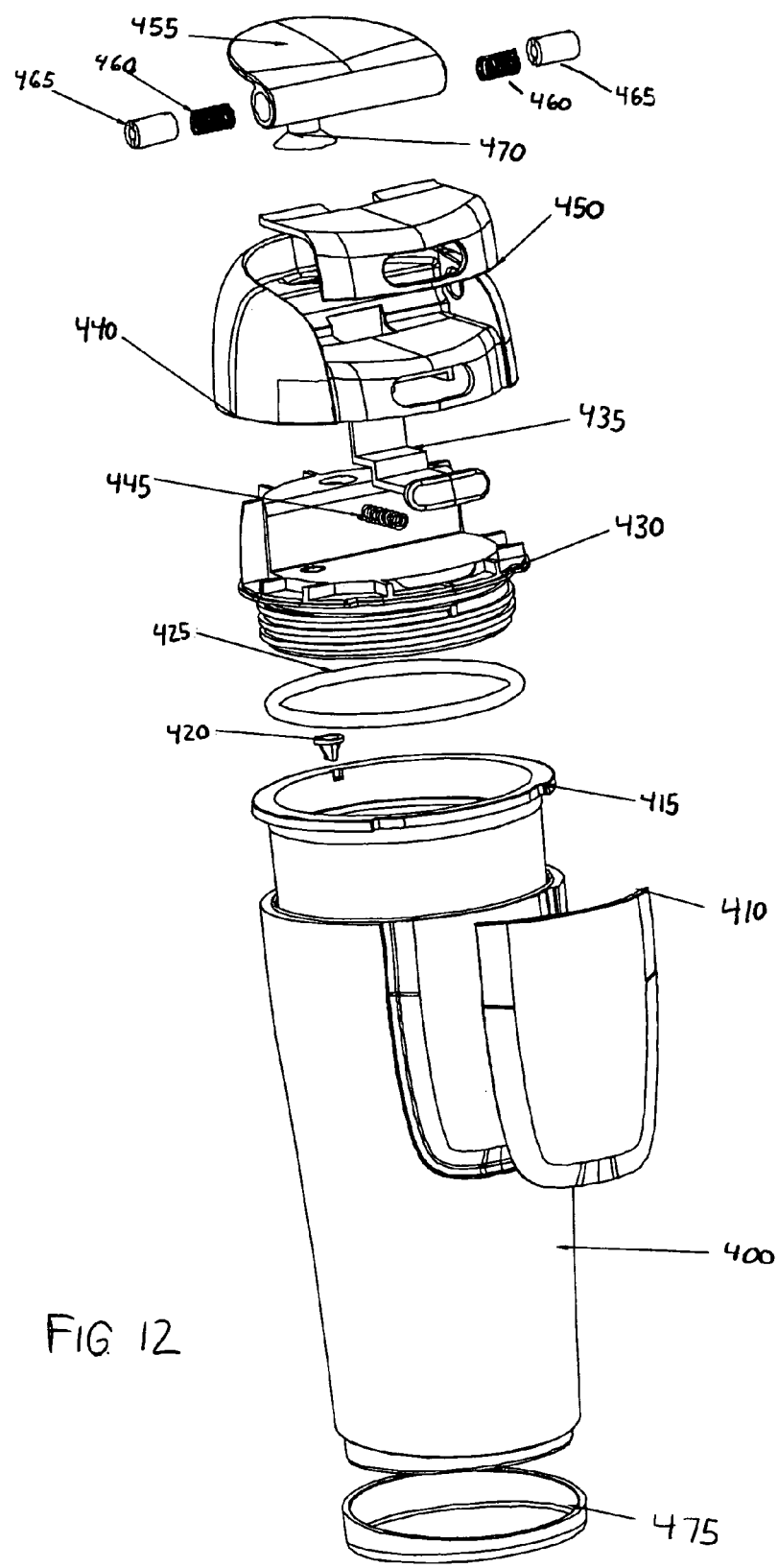
FIG. 12 is an exploded view of still another container according to another preferred embodiment of the present invention.
Figure 13:
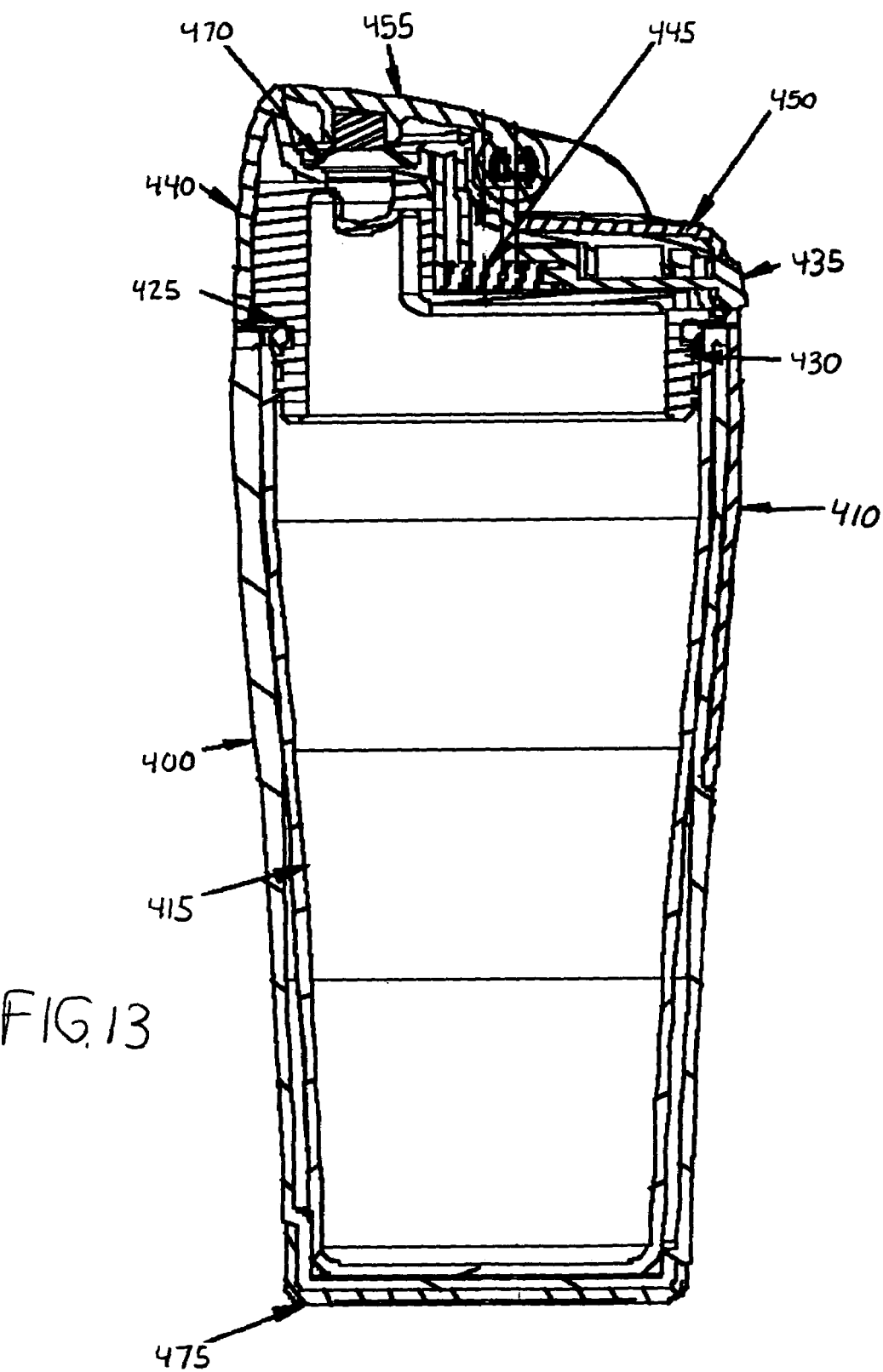
FIG. 13 is a side cross-section view of the container of FIG. 12 and its various components shown assembled.
Figure 14:
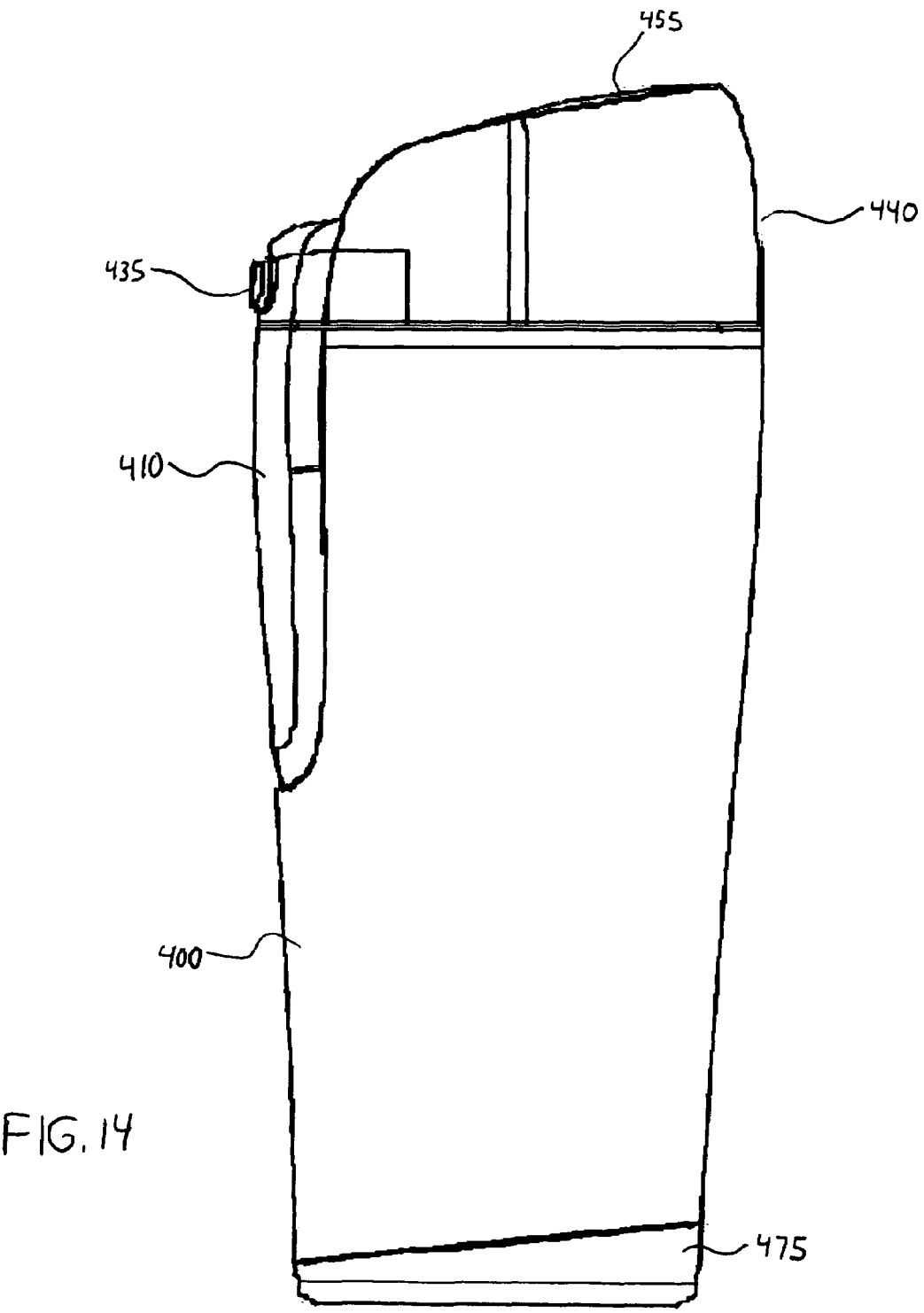
FIG. 14 is a side view of the container shown in FIGS. 12-13 with the lid in the closed position.

Reference is now made to FIGS. 12-14 which depicts still another beverage container according to a preferred embodiment of the present invention. Beverage container includes a container body 400 having a hand grip 410 and inner cup 415. The inner cup preferably contains a one-way air valve 420 for the release of hot air from beverages contained in the inner cup. This release of hot air prevents a burst of steam from hitting the user when the container is opened. The inner cup 415 contains an o-ring 425 to create a seal between the inner cup 415 and the first lid member 430. The first lid member 430 holds the activator 435 in place and connects to the second lid member 440. The activator 435 is biased in place by a spring 445 which provides the restoring force necessary to push activator 435 back into position after user depression. A third lid member 450 is attached to the second lid member 440 and holds the lid 455 in place. The lid 455 is attached to the second lid member 440 on an axis with two torsional springs 460 and hinge pins 465 which are enclosed in a hole in the lid 455. The hinge pins 465 are preferably covered in damping grease which provides damping between the lid 455 and the second lid member 440. The lid 455 preferably contains a cover 470, such as a suction member, which aids in providing an air-tight seal between the inner cup 415 and lid 455. When the activator 435 is depressed, it releases the cover 455 which is forced open on an axis by the torsional springs 460. The container body may have a bottom ring 475 to prevent the canister from slipping on a smooth surface.

While the present invention has been described with reference to the preferred embodiments, those skilled in the art will recognize that numerous variations and modifications will be made without departing from the scope of the present invention. This is especially true with regard to the specific shape and configuration of the container. Accordingly, it should be clearly understood that the embodiments of the invention described above are not intended as limitations on the scope of the invention, which is defined only by the following claims.

What is claimed is:

1. A container with controlled-opening lid comprising:
    a container body having an interior space configured and dimensioned for receiving user-supplied contents;
    a lid assembly configured and dimensioned for attachment to the container body, the lid assembly including:
        an aperture for providing access to the interior of the container body;
        a cover member configured and dimensioned to cover the aperture when in a first position and permit access to the aperture when in a second position;
        a hinge comprising a first biasing member operative to move the cover member from the first position to the second position, the hinge including a damping mechanism for damping a biasing force provided by the first biasing member when the cover member moves from the first position to the second position; and
        an activator configured and dimensioned to activate the hinge for moving the cover from the first position to the second position in response to user input, comprising a second biasing member operative to return the activator to an initial position after the user input, the second biasing member operating independently of the first biasing member.

2. The container of claim 1, wherein said damping mechanism includes damping grease.

3. The container of claim 1, wherein the activator is pivotably connected within the lid assembly.

4. The container of claim 1, further comprising a suction cup connected to a bottom surface of the cover member for covering said aperture.

5. The container of claim 1, wherein the hinge is a one-way dampening hinge.

6. The container of claim 1, wherein the lid assembly is formed of plastic, metal, or a combination of plastic and metal.

7. The container of claim 1, wherein the first biasing member is a torsional spring positioned in a first direction and the second biasing member is a spring positioned in a second direction perpendicular to the first direction.

8. The container of claim 1, further comprising a sealing ring disposed between the lid assembly and the container body.

9. The container of claim 1, wherein the container body is formed of an insulating material.

10. The container of claim 1, wherein the first biasing member includes at least one torsional spring.

11. The container of claim 1, wherein the container is a beverage container.

12. A container with controlled-opening lid comprising:
    a container body having an open end providing access to an interior space configured and dimensioned for receiving user-supplied contents;
    a lid assembly configured and dimensioned to cover the open end of the container body when in a first closed state and permit access to the interior space when in a second open state, the lid assembly including:
        a first lid member configured and dimensioned for attachment to the open end of the container body, the first lid member having a first aperture for providing access to the interior of the container body,
        a cover configured and dimensioned to cover the first aperture when in a first position and permit access to the first aperture when in a second position,
        a hinge comprising a biasing member operative to provide a biasing force to move the cover relative to the first lid member from the first position to the second position, the hinge including a damping mechanism for damping the biasing force provided by the biasing member as the cover moves from the first position to the second position; and an activator operatively disposed within the lid assembly and having an end accessible to a user through a second aperture in the lid assembly, the activator configured and dimensioned to activate the hinge for moving the cover from the first position to the second position in response to user input, wherein the activator is formed integrally with the first lid member.

13. The container of claim 12, wherein the container is a beverage container.

14. The container of claim 12, wherein said damping mechanism includes damping grease.

15. The container of claim 12, wherein the activator is pivotably connected to the first lid member.

16. The container of claim 12, wherein the biasing member includes at least one torsional spring.

17. A beverage container with controlled-opening lid comprising:
   a container body formed of an insulating material and having an open end providing access to an interior space configured and dimensioned for receiving user-supplied contents;
   a first lid member configured and dimensioned for attachment to the container body, the first lid member including at least one aperture for providing access to the interior of the container body;
   a second lid member having at least one aperture, a bottom portion of the second lid member configured and dimensioned for attachment to the first lid member;
   a cover member pivotably connected to the second lid member, the cover member configured and dimensioned to cover the aperture of the second lid member when in a first position and permit access to the aperture of the second lid member when in a second position;
   a hinge comprising a biasing member operative to provide a rotational biasing force to move the cover member relative to the second lid member from the first position to the second position, the hinge including at least one damping mechanism for damping a the biasing force provided by the biasing member when the cover member moves from the first position to the second position; and
   an activator operatively disposed on the second lid member, the activator configured and dimensioned to activate the hinge for moving the cover member from the first position to the second position in response to user input, the activator comprising a biasing member operative to provide a translational biasing force to return the activator to an initial position after the user input.

18. The beverage container of clam 17, wherein the second lid member has a second aperture, the activator accessible to a user through the second aperture.

19. The beverage container of claim 17, wherein the activator is a depressible button.

20. The beverage container of claim 17, wherein the activator biasing member is a spring.

21. The beverage container of claim 17, wherein the hinge biasing member includes at least one torsional spring.

22. The container of claim 1, wherein an exterior bottom surface of the container body includes a non-slip surface.

23. The container of claim 12, wherein an exterior bottom surface of the container body includes a non-slip surface.

24. The beverage container of claim 17, wherein an exterior bottom surface of the container body includes a non-slip surface.

25. The container of claim 1, wherein the container body comprises a one-way air valve operative to release hot air from inside the container body to prevent a burst of steam from exiting the aperture upon movement of the cover member from the first position to the second position.

26. The container of claim 17, wherein the container body comprises a one-way air valve operative to release hot air from inside the container body to prevent a burst of steam from exiting the at least one second lid member aperture upon movement of the cover member from the first position to the second position.

27. The beverage container of claim 17, wherein a bottom portion of the first lid member includes threads configured and dimensioned to mate with threads on the container body.

* * * * *